United States Patent

Patel et al.

Patent Number: 6,071,974
Date of Patent: Jun. 6, 2000

[54] LIMPID PARENTERAL SOLUTION OF 2,6-DIISOPROPHYLPHENOL AS AN ANAESTHETIC DRUG AND 2.5-DI-O-METHYL-1.4;3.6-DIANHYDRO-D-GLUCITOL AS A SOLVENT FOR MAKING CLEAR I. V. FORMULATION

[75] Inventors: Dinesh Shantilal Patel; Shashikant Prabhudas Kurani, both of Mumbai, India

[73] Assignee: Themis Chemicals Limited, India

[21] Appl. No.: 09/401,057

[22] Filed: Sep. 22, 1999

[30] Foreign Application Priority Data

Jan. 28, 1999 [IN] India ............... 65/BOM/99

[51] Int. Cl.⁷ .................. A61K 31/05; A61K 31/355; A61K 31/34
[52] U.S. Cl. ............................................. 514/731
[58] Field of Search ................... 514/731, 470, 514/458

[56] References Cited

U.S. PATENT DOCUMENTS 5,637,625  6/1997  Haynes ................... 514/731

FOREIGN PATENT DOCUMENTS

WO 98/53805  12/1998  WIPO .

Primary Examiner—Raymond Henley, III
Attorney, Agent, or Firm—Pendorf & Cutliff

[57] ABSTRACT

This invention relates to a novel pharmaceutical composition which may be administered parenterally to a mammal for the production of general anaesthesia, specifically to a limpid, stable, injectable pharmaceutical formulation of 2,6-diisopropylphenol. The formulation comprises 2,6-diisopropylphenol, a compound of the following general formula (I)

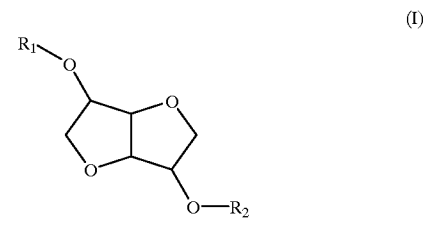

wherein $R_1$ and $R_2$ can be the same or different and are hydrogen or lower alkyl group containing 1–3 carbons or acetate group and optionally water and/or one or more antioxidants.

11 Claims, No Drawings

LIMPID PARENTERAL SOLUTION OF 2,6-DIISOPROPHYLPHENOL AS AN ANAESTHETIC DRUG AND 2.5-DI-O-METHYL-1.4;3.6-DIANHYDRO-D-GLUCITOL AS A SOLVENT FOR MAKING CLEAR I. V. FORMULATION

FIELD OF INVENTION

This invention relates to a novel pharmaceutical composition, which may be administered parenterally to a mammal for the production of general anaesthesia, specifically to a limpid, stable, injectable pharmaceutical formulation of 2,6-diisopropylphenol.

BACKGROUND OF INVENTION 2,6-diisopropylphenol is a known parenteral, short-acting general anaesthetic. It is widely used in the form of injection by anaesthetists for induction and maintenance of anaesthesia and for sedation.

Similarly, to most of the injectable anaesthetics, 2,6-diisopropylphenol has lipophilic character. This means good lipid solubility, which is necessary for the anaesthetic agent to be able to cross the blood-brain barrier. Unfortunately, the lipophilic character of the compound results that it is insoluble in and immiscible with water and thus an intravenous injection can be formulated very difficultly. Although the compound of 2,6-diisopropylphenol can be well solved in organic solvents like tetrahydrofuran, such solvents however cannot be taken into consideration for formulating a drug.

In the past efforts were made to prepare a solubilized injection. A formulation containing 2,6-diisopropylphenol and surfactant Cremophor EL® (trademark for a polyoxyethylene castor oil derivative) seemed to be acceptable but later anaphylactic reactions were reported (Laxenare MC et al, Lancet 1988 ii. 739–740).

The present commercially available formulation of 2,6-diisopropylphenol is in the form of a white, soybean oil-in-water emulsion, which is stabilized by lecithin (Diprivan). Sterile pharmaceutical compositions of 2,6-diisopropylphenol and their use in inducing anaesthesia are described in U.S. Pat. Nos. 4,056,635, 4,452,817 and 4,798,846.

There were further attempts made to prepare better formulations but all ol them were based on a kind of emulsion. Thus the U.S. Pat. No. 5,714,520 describes a composition containing edetate to prevent the growth of micro organism. It has some advantage over the currently marketed product but this is also a soybean oil-in-water emulsion with lecithin as stabilizator. The U.S. Pat. No. 5,637,625 discloses a phospholipid-coated micro-droplet formulations, which prevent the fat overload and is shown to be bactericid. The PCT Patent application No. WO 98/53805 describes a clear, injectable formulation of 2,6-diisopropylphenol with bile acid and lecithin.

These emulsion formulations have some advantages over the currently marketed formulation nevertheless certain problems arising from the emulsion form and its ingredients remained. The ingredients are natural products (soybean oil, lecithin) which require strict quality control and monitoring. They are good source, as nutrient, for growth of microorganisms, consequently strict controls for aseptic production and filling are required. Monitoring the particle size of the emulsion and keeping the product in a homogenous form as well, need complicated manufacturing technology. In a few cases hyperlipidemia caused by the fat overload in patients undergoing long term sedation was observed.

Therefore there is still a need for a stable, dose flexible anaesthetic solution, which can be conveniently filtered, sterilized and is free from all the limitations derived from the characters of emulsion formulation and its ingredients.

SUMMARY OF THE INVENTION

It has now been found that an injectable formulation of 2,6-diisopropylphenol may be obtained by dissolving 2,6-diisopropylphenol in an isosorbide type solvent characterized by the following general formula (I)

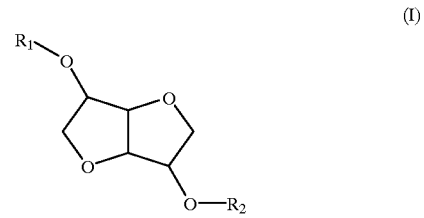

(I)

wherein $R_1$ and $R_2$ can be the same or different and are hydrogen or alkyl group containing 1–3 carbons or acetate group. The formulation optionally comprises water and/or one or more antioxidants.

The solution obtained is clear, limpid and can be conveniently administered intravenously, with flexibility of a dose pending to the need of the patient. The formulation is stable, safe and as effective as the currently marketed formulation.

Preferably, the formulation is prepared by dissolving 2,6-diisopropylphenol in a mixture of the said isosorbide type solvent and water.

The addition of the antioxidants like alpha-tocopherol and its derivatives the formulation enhances the stability of the solution. The pH of the solution obtained can be adjusted to neutral by the addition of sodium hydroxide. The pH may also be buffered to a level of between about 5.0 and 8.5.

The present invention also relates to a process for manufacturing of the pharmaceutical composition which comprises 2,6-diisopropylphenol and a compound of general formula (I)

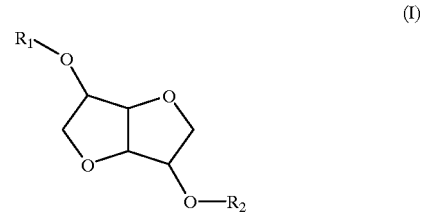

(I)

wherein $R_1$ and $R_2$ can be the same or different and are hydrogen or lower alkyl group containing 1–3 carbons or acetate group and optionally water and/or one or more antioxidants, the process comprising adding 2,6-diisopropylphenol and optionally one car more antioxidants to a compound of general formula (I) as defined above and if desired adjusting the pH of the solution so obtained.

The present invention further relates to the use of pharmaceutical composition for induction and maintenance of anaesthesia and for sedation in mammals which composition comprises 2,6-diisopropylphenol and a compounds of general formula (I)

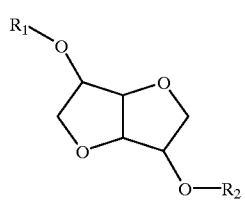

(I)

wherein $R_1$ and $R_2$ can be the same or different and are hydrogen or lower alkyl group containing 1–3 carbons or acetate group and optionally water and/or one of more antioxidants.

The compound of formula 1 is preferably 2,5-di-O-methyl-1,4:3,6-dianhydro-D-glucitol.

DETAILS OF THE INVENTION

The compounds of general formula (I) in an anaesthetic composition serve as excellent and convenient solvents for the 2,6-diisopropylphenol. It has been found that the solubility of 2,6-diisopropylphenol in the compounds of general formula (I) is very satisfactory. It can be allowed to produce products in various concentrations i.e., injections with various strengths. Thus the injections can be used immediately in the appropriate strength, without any further dilution which makes easier the work of the medical practitioners. We have prepared formulations in the mostly used strengths i.e., 5,10,50 and 100 mg/ml. Injections of any kind of strengths can be prepared very easily.

We have made further experiments to ascertain whether the formulation according to the invention can dilute with water. It has been found that formulations obtained by dissolving 2,6-diisopropylphenol in mixture of water and isosorbide type solvent are as stable, clear and homogenous as the formulations in which only isosorbide type solvent was used as solvent. The experiments have shown that the dilution of a compound of general formula (I) with water up to 20% water content by volume of the total composition has no effect on the characteristics of the original formulation.

The effectiveness of the formulation according to the invention has been studied on mice, dogs and pigs in laboratories. The study has shown that the formulation according to the invention is a potent inducer of anaesthesia with practically no side effects for internal use.

The duration of anaesthesia generated by the currently marketed emulsion formulation and the formulation according to the invention were compared. The experiments were carried out on Swiss mice. It has been found that the duration of anaesthesia was longer in the case of formulation according to the invention than in the case of currently marketed emulsion formulation. The mice were observed for further 96 hours after the experiment and there were no visible adverse effects on them. The results of the experiment are shown below in Table 1.

TABLE 1

Comparative study on loss of righting effect

| Product | Concentration (mg/ml) | No. of Mice | Duration of Anaesthesia (min.) |
|---|---|---|---|
| I. Emulsion formulation (Market sample) | 16.6. | 6 | 2.53 |
| II. Clear invented composition | | | |
| (A) | 16.6 | 6 | 4.52 |
| (B) | 16.6 | 6 | 5.42 |

After having seen the effect of the initial induction of anaesthetic effect, further studies were carried out. Three-three beagle dogs were treated with injection of the currently marketed emulsion formulation and the formulation according to the invention in a dose of 2 mg/kg. Blood pressure, respiration, pulse and temperature of the animals were measured before and after the injection. The time of induction and recovery after initial administration were measured. The following parameters were studied: dilation of pupils, sedation, pinch reflexes, peddle reflexes at the time of anaesthesia.

It could be observed that the onset of action of formulation according to the invention was comparable and effect of the drug is slightly better as compared to the currently marketed emulsion formulation. The physiological parameters during anaesthesia remained unaltered, before and after injection. The blood profile has also shown no changes when compared with initial studies.

The dogs were observed over a period of 72 hours after the experiments, to check any adverse effect of anaesthesia. The observation revealed no adverse/abnormal effect or behaviour. The results of the experiments are shown in Table 2-A and 2-B.

TABLE 2-A

Experiments for induction of anaesthesia in dogs
Emulsion formulation (market composition of 2,6-diisopropylphenol)
Dose: 2 mg/kg wt.

| Animal | Effects | Blood pressure | Temperature [° F.] | Respiration [1/min] | Pulse [1/min] | Body reflexes |
|---|---|---|---|---|---|---|
| Dog 1 | Slight sedation Calming at 5 Minutes | 120/90 | 102.0 | 40 | 54 | Neck movement and pain reflexes. |
| Dog 2 | Slight sedation Sleeping after 10 Minutes | 110/90 | 102.0 | 45 | 60 | Neck movement and pain |

TABLE 2-A-continued

Experiments for induction of anaesthesia in dogs
Emulsion formulation (market composition of 2,6-diisopropylphenol)
Dose: 2 mg/kg wt.

| Animal | Effects | Blood pressure | Temperature [° F.] | Respiration [1/min] | Pulse [1/min] | Body reflexes |
|---|---|---|---|---|---|---|
| Dog 3 | Sedation in 30 secs up to 3 minutes. Recovery: head lift to ataxia 7 mins. | 120/90 | 101.5 | 50 | 62 | Relaxed, no pain reflexes |

TABLE 2-B

Experiments for induction of anaesthesia in dogs
Clear formulation according to the invention
Dose: 2 mg/kg wt.

| Animal | Effects | Blood pressure | Temperature [° F.] | Respiration [1/min] | Pulse [1/min] | Body reflexes |
|---|---|---|---|---|---|---|
| Dog 4 | Sedation in 30 seconds lasted for 4.5 minutes Recovery: head lift to ataxia $6^{th}$ min. | 120/96 | 102.0 | 45 | 53 | Relaxed |
| Dog 5 | Sedation in 30 seconds lasted for 3.5 minutes Recovery: head lift to ataxia $6^{th}$ min. | 110/90 | 102.0 | 45 | 60 | Relaxed |
| Dog 6 | Slight sedation Sleeping after 4 to 5 mins. Recovery: head lift to ataxia $6^{th}$ min. | 120/90 | 102.0 | 44 | 58 | Neck movement |

Experiments were carried out to study the anaesthetic activity and the maintenance of anaesthesia on male European pigs. These experiments showed that the formulation according to the invention shows comparable activity for induction, maintenance and recovery of anaesthesia. There were no unexpected adverse reactions as compared to the currently marketed formulation.

Repeated injections of the formulation according to the invention, when given intravenously to the pig, did not give rise to any hypersensitivity reactions. There was no bronchospasm, tachycardia, respiratory distress or cardiac arrest observed. Recovery from anaesthesia was smooth with no excitatory reactions.

Blood profile was monitored before, during and after injection. The results showed that no significant changes took place in case of both of the compositions.

The pigs were observed for 72 hours post anaesthesia and neither anaphylactic reactions nor abnormal signs were detected.

The results of the experiments are shown below in Table 3 and Table 4.

TABLE 3

Comparative Anaesthetic Activity of the Clear Formulations According to the Invention on Pigs (n-6)
Single Dose Study

| Activity | EMULSION FORMULATION | | | | | | CLEAR INVENTED COMPOSITION | | | | | |
|---|---|---|---|---|---|---|---|---|---|---|---|---|
| | Animal 1 (Wt. 21 kgs.) | | Animal 2 (Wt. 25 kgs.) | | Animal 3 (Wt. 22.5 kgs.) | | Animal 1 (Wt. 23 kgs.) | | Animal 2 (Wt. 27 kgs.) | | Animal 3 (Wt. 19 kgs.) | |
| Induction Anaesthesia (min) | 6.5 | | 6.6 | | 6.4 | | 7.0 | | 6.9 | | 7.1 | |
| Head lift to Ataxia (min) | 22 | | 21 | | 20 | | 25 | | 27 | | 26 | |
| | Before Injection | After Injection | Before Injection | After Injection | Before Injection | After Injection | Before Injection | After Injection | Before Injection | After Injection | Before Injection | After Injection |
| Temperature (° F.) | 101.0 | 101.0 | 99.9 | 98.5 | 97.0 | 98.0 | 101.0 | 100.0 | 100.0 | 99.5 | 101.0 | 100.0 |
| Pulse (1/min) | 94 | 96 | 95 | 95 | 85 | 85 | 87 | 87 | 90 | 87 | 85 | 85 |

TABLE 3-continued

Comparative Anaesthetic Activity of the Clear Formulations According to the Invention on Pigs (n-6)
Single Dose Study

| Respiration (1/min) | 22 | 20 | 23 | 23 | 19 | 20 | 19 | 18 | 21 | 20 | 19 | 19 |
|---|---|---|---|---|---|---|---|---|---|---|---|---|
| Dose | | | Animal 1 | 8.6 mg/kg in 30 seconds | | | | | | | | |
| | | | Animal 2 | 7.2 mg/kg in 30 seconds | | | | | | | | |
| | | | Animal 3 | 8.0 mg/kg in 30 seconds | | | | | | | | |

INTERMITTANT INJECTION (AFTER LOADING DOSE)

| | EMULSION FORMULATION | | | CLEAR INVENTED COMPOSITION | | |
|---|---|---|---|---|---|---|
| | Animal 1 | Animal 2 | Animal 3 | Animal 1 | Animal 2 | Animal 3 |
| Induction Time (min) | 6.4 | 7.0 | 6.8 | 7.5 | 8.0 | 7.8 |
| Sleeping Time (min) | 25 | 30 | 35 | 21 | 30 | 28 |
| Total Recovery (min) | 30 | 35 | 25 | 30 | 38 | 33 |
| Dose | Animal 1, Animal 2 and Animal 3: 10 mg/min in both Emulsion Formulation & Clear Invented Composition | | | | | |

TABLE 4

MAINTENANCE OF ANAESTHESIA

| | EMULSION FORMULATION | | | CLEAR INVENTED COMPOSITION | | |
|---|---|---|---|---|---|---|
| | Animal 1 | Animal 2 | Animal 3 | Animal 1 | Animal 2 | Animal 3 |
| Maintenance of Anaesthesia (min) | 45 | 50 | 55 | 60 | 40 | 45 |
| Recovery Time (min) | 5.0 | 5.5 | 5.0 | 6.0 | 6.2 | 5.0 |

The formulation according to the invention has been found to be stable. In the stability study samples of the clear formulation according to the inventions with and without pH adjustment and with and without adding antioxidant(s) were tested. The pH adjustment was carried out by 0.1 M sodium hydroxide, filling and sealing in amber vials. The used antioxidant was alpha-tocopherol (Vitamin E). The study was carried out at room temperature in normal storage conditions. The stability of the currently marketed emulsion formulation was also checked in same conditions. The 2,6-diisopropylphenol content was measured by Isocratic, GBC make HPLC equipment ($C_{18}$ column, 270 nm, 20 $\mu$l injection volume). The result of the experiments are shown below in Table 5-A and 5-B.

TABLE 5-A

Stability test - Clear invented composition
concentration: 10 mg/ml; pH = 7.0
Results in % of the theoretic amount of 2,6-diisopropylphenol
(10 mg/ml)

| | Initial | | 3 months, room temp. | | 3 months 40° C., 60% RH | |
|---|---|---|---|---|---|---|
| Sample | With Vitamin E | Without Vitamin E | With Vitamin E | Without Vitamin E | With Vitamin E | Without Vitamin E |
| A | 98.9 | 99.0 | 98.8 | 99.1 | 98.5 | 97.5 |
| B | 99.3 | 99.6 | 99.6 | 99.5 | 97.5 | 96.8 |
| C | 100.3 | 101.0 | 100.1 | 100.0 | 93.5 | 94.5 |

RH = Relative Humidity

TABLE 5-B

Stability test - Emulsion formulation
concentration: 10 mg/ml; pH = 7.0
Results in % of the theoretic amount of 2,6-diisopropylphenol
(10 mg/ml)

| Sample | Initial | 3 months, room temp. | 3 months 40° C., 60% RH |
|---|---|---|---|
| A | 99.0 | 98.6 | 98.2 |
| B | 100.1 | 98.5 | 98.2 |
| C | 99.8 | 97.5 | 97.3 |

RH = Relative Humidity

EXAMPLE 1

2.8 mmol of 2,6-diisopropylphenol is added to 100 ml 2,5-di-O-methyl-1,4:3,6-dianhydro-D-glucitol with stirring. The solution is stirred further for 15 minutes in aseptic condition. The pH was measured potentiometrically and found 5.3 without adjusting. The solution filtered aseptically and then filled and sealed in vial/ampoule.

EXAMPLE 2

2.8 mmol of 2,6-diisopropylphenol is added to 80 ml 2,5-di-O-methyl-1,4:3,6-dianhydro-D-glucitol with stirring. The solution is stirred further for 15 minutes in aseptic condition. The pH is adjusted by 0.1 M sodium hydroxide to 7. The solution is diluted to 100 ml with 2,5-di-O-methyl-1,4:3,6-dianhydro-D-glucitol and filtered aseptically, filled and then sealed in containers.

EXAMPLE 3

2.8 mmol of 2,6-diisopropylphenol and 0.116 mmol (0.05% by w/v) alpha-tocopherol arc added to 100 ml 2,5-di-O-methyl-1,4:3,6-dianhydro-D-glucitol with stirring. The solution is stirred further for 15 minutes in aseptic condition. The pH was measured potentiometrically and found 5.35 without adjusting. The solution filtered aseptically and then filled and sealed in vial/ampoule.

EXAMPLE 4

2.8 mmol of 2,6-diisopropylphenol and 0.232 mmol (0.1% by w/v) alpha-tocopherol are added to 100 ml 2,5-di-O-methyl-1,4:3,6-dianhydro-D-glucitol with stirring. The solution is stirred further for 15 minutes in aseptic condition. The pH was measured potentiometrically and found 5.4 without adjusting. The solution filtered aseptically and then filled and sealed in vial/ampoule.

EXAMPLE 5

2.8 mmol of 2,6-diisopropylphenol and 0.116 mmol (0.05% by w/v) alpha-tocopherol are added to 80 ml 2,5-di-O-methyl-1,4:3,6-dianhydro-D-glucitol with stirring. The solution is stirred further for 15 minutes in aseptic condition. The pH is adjusted by 0.1 M sodium 1s hydroxide to 7. The solution is diluted to 100 ml with 2,5-di-O-methyl-1,4:3,6-dianhydro-D-glucitol and filtered aseptically, filled and then sealed in containers.

EXAMPLE 6

2.8 mmol of 2,6-diisopropylphenol and 0.232 mmol (0.1% by w/v) alpha-tocopherol are added to 80 ml 2,5-di-O-methyl-1,4:3,6-dianhydro-D-glucitol with stirring. The solution is stirred further for 15 minutes in aseptic condition. The pH is adjusted by 0.1 M sodium hydroxide to 7. The solution is made to 100 ml with 2,5-di-O-methyl-1,4:3,6-dianhydro-D-glucitol and filtered aseptically, filled and then sealed in containers.

EXAMPLE 7

5.61 mmol of 2,6-diisopropylphenol is added to 100 ml 2,5-di-O-methyl-1,4:3,6-dianhydro-D-glucitol with stirring. The solution is stirred further for 15 minutes in aseptic condition. The pH was measured potentiometrically and found 5.3 without adjusting. The solution filtered aseptically and then filled and sealed in vial/ampoule.

EXAMPLE 8

28.04 mmol of 2,6-diisopropylphenol is added to 100 ml 2,5-di-O-methyl-1,4:3,6-dianhydro-D-glucitol with stirring. The solution is stirred further for 15 minutes in aseptic condition. The pH was measured potentiometrically and found 5.3 without adjusting. The solution filtered aseptically and then filled and sealed in vial/ampoule.

EXAMPLE 9

56.09 mmol of 2,6-diisopropylphenol is added to 100 ml 2,5-di-O-methyl-1,4:3,6-dianhydro-D-glucitol with stirring. The solution is stirred further for 15 minutes in aseptic condition. The pH was measured potentiometrically and found 5.3 without adjusting. The solution filtered aseptically and then filled and sealed in vial/ampoule.

What is claimed is:

1. A pharmaceutical composition which comprises 2,6-diisopropylphenol and a compound of general formula (I)

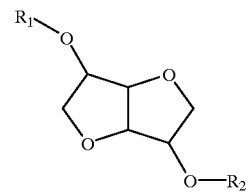

(I)

wherein $R_1$ and $R_2$ can be the same or different and are hydrogen or lower alkyl group containing 1–3 carbons or acetate group and optionally water and/or one or more antioxidants.

2. Composition according to claim 1 wherein the said compound of general formula (I) is 2,5-di-O-methyl-1,4:3,6-dianhydro-D-glucitol.

3. Composition according to claim 1 wherein the concentration of 2,6-diisopropylphenol is 1–500 mg/ml of composition.

4. Composition according to claim 1 wherein the amount of water is no more than 20% by volume of said composition.

5. Composition according to claim 1 wherein said antioxidant or antioxidants can be selected from the group consisting alpha-tocopherol and its derivatives.

6. Composition according to claim 1 which is buffered to a pH of between about 5.0 and about 8.5.

7. A sealed sterile ampoule or vial or bottle containing the sterile pharmaceutical composition as claimed in claim 1.

8. Process for manufacturing of the pharmaceutical composition which comprises 2,6-diisopropylphenol and a compounds of general formula (I)

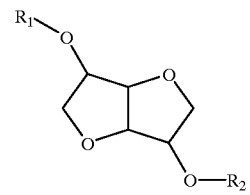

(I)

where $R_1$ and $R_2$ can be the same or different and are hydrogen or lower alkyl group containing 1–3 carbons or acetate group and optionally water and/or one or more antioxidants, comprising adding 2,6-diisopropylphenol and optionally one or more antioxidants to a compound of general formula (I) as defined above and if desired adjusting the pH of the solution obtained.

9. Process according to claim 8 wherein said compound of general formula (I) is 2,5-di-O-methyl-1,4:3,6-dianhydro-D-glucitol.

10. Method for induction and maintenance of anaesthesia and for sedation in mammals, which method comprises administering to said mammal an effective amount of 2,6-diisopropylphenol and at least one compound of general formula (I)

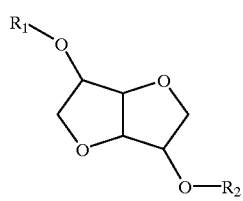 (I)
wherein $R_1$ and $R_2$ can be the same or different and are hydrogen or lower alkyl group containing 1–3 carbons or acetate group and optionally water and optionally one or more antioxidants.
11. Method according to claim 10, wherein said compound of general formula (I) is 2,5-di-O-methyl-1,4:3,6-dianhydro-D-glucitol.
* * * * *